US006488829B1

United States Patent
Schroeder et al.

(10) Patent No.: US 6,488,829 B1
(45) Date of Patent: Dec. 3, 2002

(54) HIGH-THROUGHPUT ELECTROPHYSIOLOGICAL MEASUREMENT APPARATUS

(76) Inventors: Kirk S. Schroeder, 4103 Lake Forest Dr. West, Ann Arbor, MI (US) 48108; Bradley D. Neagle, 5415 Vorhies Rd., Ann Arbor, MI (US) 48103

(*) Notice: Subject to any disclaimer, the term of this patent is extended or adjusted under 35 U.S.C. 154(b) by 46 days.

(21) Appl. No.: 09/631,909

(22) Filed: Aug. 4, 2000

Related U.S. Application Data

(60) Provisional application No. 60/147,253, filed on Aug. 5, 1999, and provisional application No. 60/176,698, filed on Jan. 18, 2000.

(51) Int. Cl.[7] .......................................... G01N 27/416
(52) U.S. Cl. ........................ 204/403.01; 435/287.1; 422/63; 422/65
(58) Field of Search ................... 204/403, 403.01; 435/287.1, 287.5, 817; 422/63, 65

(56) References Cited

U.S. PATENT DOCUMENTS

| | | | |
|---|---|---|---|
| 4,055,799 A | * 10/1977 | Coster et al. | 204/403 |
| 4,894,343 A | * 1/1990 | Tanaka et al. | 210/498 |
| 6,063,260 A | 5/2000 | Olesen et al. | 205/793 |
| 6,267,872 B1 | * 7/2001 | Akeson et al. | 204/409 |
| 6,284,113 B1 | * 9/2001 | Bjornson et al. | 204/450 |
| 6,315,940 B1 | * 11/2001 | Nisch et al. | 204/403 |

FOREIGN PATENT DOCUMENTS

WO   WO 99/66329   12/1999

* cited by examiner

Primary Examiner—Robert J. Warden, Sr.
Assistant Examiner—Kaj K. Olsen
(74) Attorney, Agent, or Firm—Gifford, Krass, Groh, Sprinkle, Anderson & Citkowski, PC

(57) ABSTRACT

Standard electrophysiology via the patch clamp technique is a well-developed and powerful tool in both academic and industrial research in the study of ion channels and transporters. Although widely accepted as the gold standard for these types of measurements, the patch clamp technique is considered labor intensive and relatively slow, limited to measuring only one biological sample at a time. This invention describes and demonstrates a device whereby electrophysiological measurements can be made on cells or cell membranes in a manner which allows for multiple measurements to be made in parallel, without direct human intervention, thereby enhancing the cost effectiveness, throughput and general applicability of the technique in fields such as pharmaceutical drug screening.

45 Claims, 7 Drawing Sheets

HIGH-THROUGHPUT ELECTROPHYSIOLOGICAL MEASUREMENT APPARATUS

REFERENCE TO RELATED APPLICATION

This application claims priority from U.S. provisional patent application Ser. No. 60/147,253, filed Aug. 5, 1999 and No. 60/176,698, filed Jan. 18, 2000, the entire contents of both of which are incorporated herein by reference.

FIELD OF THE INVENTION

The present invention relates generally to the field of electrophysiology, wherein electrical measurements are made on biological cells and cell membranes to understand interactions between specific membrane components such as ion channels and transporters. Such measurements may be performed on living cells, membranes, or vesicles, as well as artificial membranes. More particularly, the invention resides in methods and apparatus enabling electrophysiological measurements to be made in parallel, without direct human intervention, thereby enhancing the cost effectiveness, throughput and general applicability of the technique to pharmaceutical drug screening and other procedures.

BACKGROUND OF THE INVENTION

The electrical behavior of cells and cell membranes is of profound importance in basic research as well as in modern drug development. A specific area of interest in this field is in the study of ion channels and transporters [1]. Ion channels are protein-based pores found in the cell membrane that are responsible for maintaining the electro-chemical gradients between the extra cellular environment and the cell cytoplasm. Quite often these membrane channels are selectively permeable to a particular type of ion, e.g. potassium or sodium. The channel is generally comprised of two parts; the pore itself, and a switch mechanism that regulates the conductance of the pore. Examples of regulation mechanisms include changes in transmembrane voltage or the activation or deactivation of a membrane receptor via a chemical ligand. Ion channels are passive elements in that once opened, ions flow in the direction of existing chemical gradients. Ion transporters are similar in that they are involved in the transport of ions across the cell membrane, however they differ from ion channels in that energy is required for their function and they tend to actively pump against established electrochemical gradients.

Ion channels are prevalent in the body and are necessary for many physiological functions including the beating of the heart, voluntary muscle contraction and neuronal signaling. They are also found in the linings of blood vessels allowing for physiological regulation of blood pressure and in the pancreas for control of insulin release. As such, the study of such channels is a very diverse and prolific area encompassing basic academic research as well as biotech and pharmaceutical research. Experiments on ion channels are typically performed on cell lines with endogenously express the ion channel of interest ("native channels") as well as on recombinant expression systems such as the Xenopus Oocyte or mammalian cell lines (e.g. CHO, HEK etc.) where the channels are inserted by well-known transfection techniques [2] [3]. Electrophysiology is also performed on isolated cell membranes or vesicles as well as in synthetic membranes where solubilized channels are reconstituted into a manufactured membrane [4].

To date, the most useful and widely utilized tool for the study of ion channels and transporters is via a technique called patch clamping. This technique was first introduced almost 25 years ago [5] [6] [7], and consists of using a small glass capillary to function as an electrode in measuring currents and voltages from individual cells. FIG. 1 depicts a typical patch clamp measurement geometry. A glass capillary 2 is first heated and pulled to a fine tip. The capillary is then filled with a saline buffer solution 4 and fitted with a Ag/AgCl electrode 6. The function of the Ag/AgCl electrode is to provide an electrical connection to a wire via the reversible exchange of chloride ions in the pipette solution.

Through the use of a microscope and micromanipulating arm (not shown), the user finds a biological cell or cell membrane 8 containing ion channels 10 of interest and gently touches the cell membrane with the pipette. The measurement circuit is complete via the external ionic solution 12 and a second Ag/AgCl bath electrode 14. A high-impedance operational amplifier 16 senses the current flowing in the circuit which is subsequently recorded and analyzed with a data recording system 18. The key to the function of the technique is the ability to form a high electrical resistance (~1GΩ) seal between the glass pipette and the cell membrane 20, so that the current recorded by the amplifier is dominated by ions 22 flowing through the cell membrane and not ions flowing around the glass pipette directly into the bath solution.

Once a high-resistance seal is achieved between the pipette and the cell membrane, there are many measurement configurations that the system can take, the scope of which is beyond this disclosure. One of the more common is the whole cell voltage clamp. In this configuration it is necessary to permeabilize the portion of membrane at the end of the pipette 24 so as to effectively place the pipette electrode inside the cell. This in turn allows for an external voltage command 26 to be placed between the intracellular pipette electrode and the extracellular bath electrode, thereby providing control of the cell's transmembrane voltage potential. The term "whole cell" is derived from the fact that with this configuration, the instrument measures the majority of the currents in the entire cell membrane.

The electrical permeabilization of the membrane at the end of the pipette can be induced in many ways but is often achieved by voltage pulses of sufficient strength and duration such that the membrane inside the pipette physically breaks down. This is commonly referred to as "zapping" [8] and is a well-known technique in the field. Another technique utilized to electrically permeabilize the membrane is through the use of certain antiobiotics such as Nystatin and Amphotericin B [9]. These chemicals work by forming chemical pores in the cell membrane that are permeable to monovalent ions such as chloride. Since chloride is the current carrying ion for the commonly used Ag/AgCl electrode, these antiobiotics can produce a low resistance electrical access to the interior of the cell. The advantage of the chemical technique is that the membrane patch remains intact such that larger intracellular molecules remain inside the cell and are not flushed out by the pipette solution as with the zapping technique. The use of chemicals to electrically permeabilize the membrane is also a commonly used technique in the field and is referred to as a "perforated patch" [8] [9][10].

The formation of the high-resistance electrical seal enables the measurement system to detect very small physiological membrane currents, (e.g. $10^{-12}$ amp). In addition, by perforating a portion of the cell membrane either electrically or chemically, it possible to control the voltage (voltage clamp) or current (current clamp) across the remaining intact portion of the cell membrane. This greatly enhances the utility of the technique for making physiological measurements of ion channel/transporter activity since quite often this activity is transmembrane voltage dependent. By being able to control the trans-membrane voltage (or current), it is possible to stimulate or deactivate ion channels or transporters with great precision and as such greatly enhance the ability to study complex drug interactions.

The development of the patch clamp technique revolutionized the field allowing for the direct electrical measurement of ion channel/transporter events in living cells, cell membranes and artificial membranes. However, existing patch clamp techniques require the use of a skilled operator using a microscope and micromanipulating arm to record data from a single cell or membrane preparation using a small glass capillary. Typically, a recording session may take tens of minutes to complete and requires a high level of dexterity by the operator. In addition, especially in the case of drug screening, it is generally preferable to obtain a new cell sample for each different chemical entity to be tested. As such, the technique is not relevant to looking at thousands of different conditions (e.g. chemical stimuli) per day, a common need in the biotech or pharmaceutical industry.

U.S. Pat. No. 6,063,260 to Olesen describes a system intended to improve the throughput and decrease the fluid volume required of standard patch clamp technology. The improvement relies on using a standard HPLC autosampler apparatus integrated into a standard patch clamp arrangement in order to more easily inject multiple fluids samples into the measurement system. The invention claims to increase throughput by making multiple sequential fluid additions to the same biological membrane faster and easier. However, the Oleden invention is deficient in several respects. First, it does not allow for a plurality of different biological samples to be measured simultaneously. In addition, it does not eliminate the labor intensive aspects of micromanipulation involved in standard patch clamp electrophysiology, nor does it address cases in biological drug screening where multiple chemical reagent additions to the same biological sample are to be avoided (as in the case of high-throughput drug screening).

Published PCT Application WO 99/66329 discusses the use of a perforated screen to conduct tests on biological materials, but is clear from the disclosure that the proposed system presents significant severe limitations in terms of a practical implementation. First, all embodiments discussed in the WO 99/66329 application utilize multiple apertures per fluid well, placing reliance on the growth of confluent cell matrices to effectuate sealing of the multiple perforations formed in relatively thick material. In addition, although the published application makes reference to automation, no workable, fully integrated systems are disclosed which are capable of high throughput and reliability.

SUMMARY OF THE INVENTION

In broad and general terms, the invention described enables electrophysiological measurements to be made more quickly than with standard patch clamp techniques. The invention uses a thin, preferably layered substrate having a properly sized hole, on the order of a few microns in diameter, allowing a cell or biological membrane to be maneuvered by fluid flow to the hole independent of direct human intervention, thereby eliminating the use of a microscope and micromanipulating arm. This approach not only makes the measurement easier, it also provides a platform by which a plurality of measurements can be made simultaneously, greatly improving measurement throughput.

Through proper selection and processing of the substrate material, hole geometry, and attention to the way in which the biological membrane interacts with the substrate, a high-resistance electrical seal on the order of several hundred MΩ to 1 GΩ is achieved. Preferred substrates include thin plastic films in which small holes have been photomachined using a laser. These substrates were then vacuum deposited with thin layers of glass in order to aid in the formation of the high-resistance seal. Silicon substrates are also described, wherein standard photolithographic/wet etching techniques are to make the holes. In both cases, individual cells are then positioned onto isolated holes using differential pressure.

The invention further contemplates a substrate geometry which is directly applicable to the development of a high-throughput instrument whereby thousands of single cell electrophysiological recordings could be acquired in a single day. In addition, the invention encompasses an integrated electrophysiogical measurement system which includes a computer controlled data collection system, an integrated electronics head for making parallel electrical measurements, and an integrated fluidics head used in part to transfer test compounds into the measurement process.

DETAILED DESCRIPTION OF THE INVENTION

In contrast to standard patch clamp techniques, wherein a glass pipette is used to form a high-resistance electrical seal with a biological membrane, this invention preferably utilizes a single, small hole in a substrate to provide the sealing function. One advantage of this approach is that it eliminates the need for micromanipulation by a skilled user, while providing a format suitable for achieving multiple electrical seals in parallel, thereby increasing the measurement throughput of the device.

Figure 1:
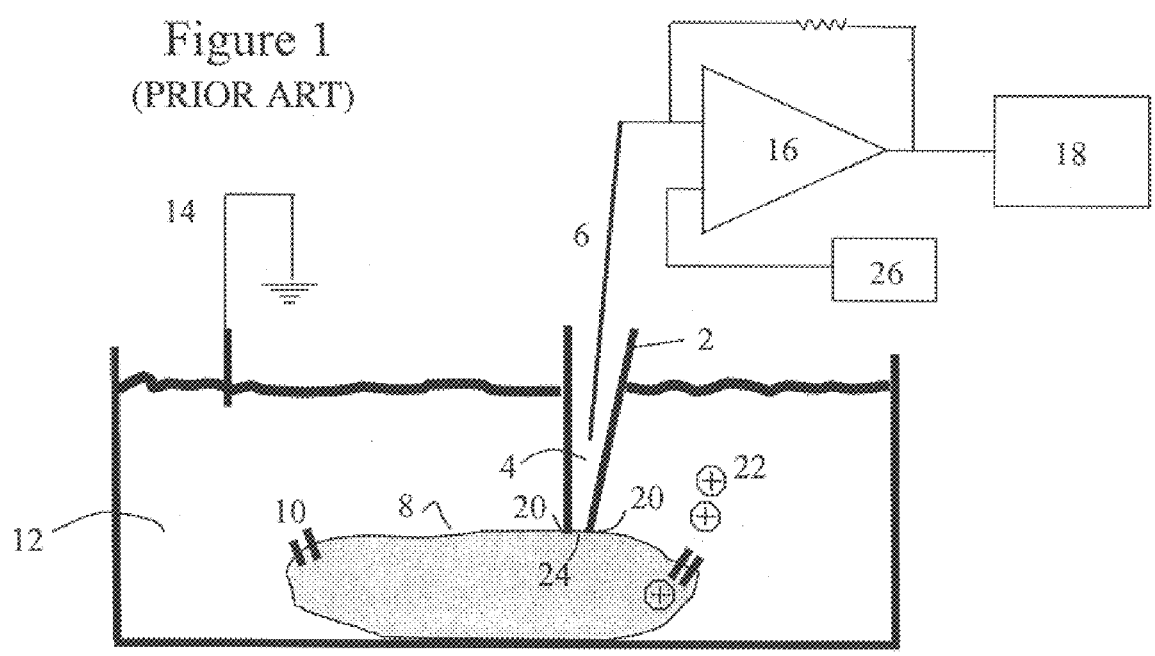
FIG. 1 is a prior-art patch clamp electrophysiology configuration showing measurement geometry.
Figure 2:
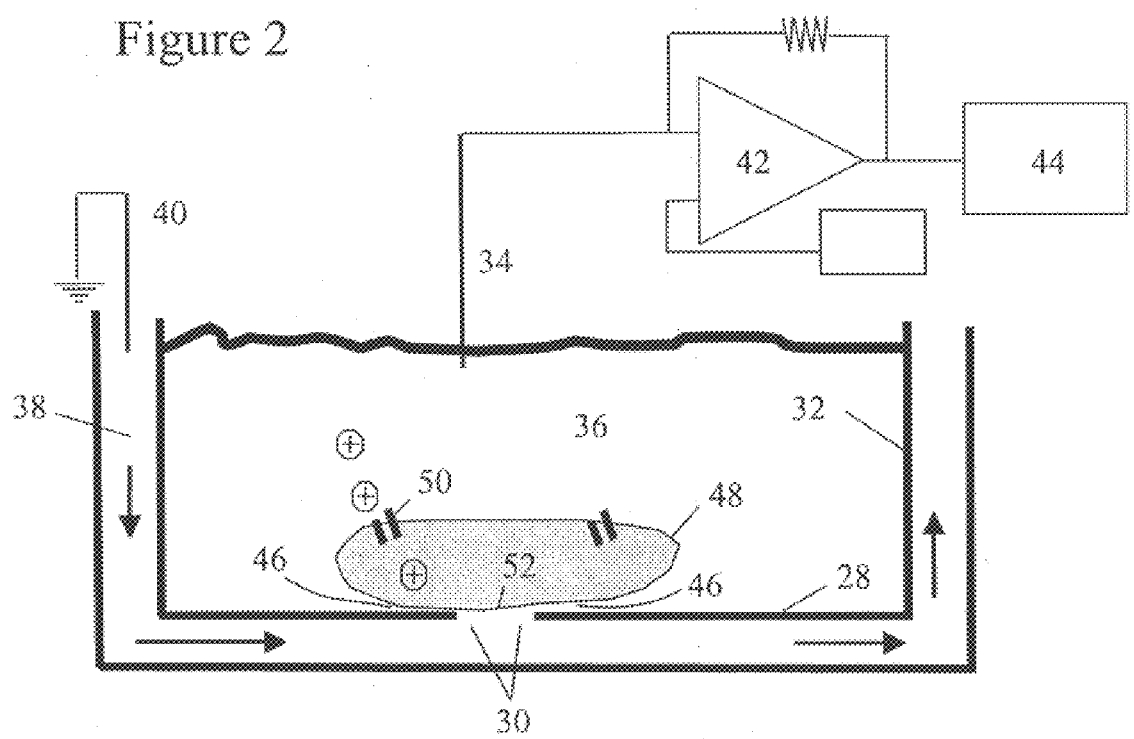
FIG. 2 depicts the formation of an electrical seal between a single cell and a single hole in a substrate according to the invention.

FIG. 2 depicts a measurement geometry with respect to the invention for a single measurement chamber. Starting with a thin (<25 μm thickness) substrate 28, a single hole 30

(~2 to 4 μm diameter) is formed in the bottom of the chamber 32. An electrical circuit is implemented through the use of Ag/AgCl sensing electrode 34 in contact with an ionic saline solution 36. A second isolated fluid chamber 38 allows fluid access to the bottom side of the hole 30 in conjunction with a bath electrode 40, thereby completing the measurement circuit. The current flowing in the circuit is sensed by a high-impedance operational amplifier 42 and recorded by a computer controlled data acquisition system 44.

An important aspect of the invention is the ability to form an electrical seal 46 between the surface of the substrate 28 and the biological membrane 48 without micromanipulation by a skilled technician. To achieve this, the cell is placed in suspension in the top chamber 36, and drawn to the hole 30 through the use of differential pressure applied between the bottom chamber 38 and the top chamber 36. It has been found and demonstrated that once a cell reaches a properly chosen and engineered substrate, an electrical seal of several hundred MΩ to greater than 1 GΩ is achievable. Given this high seal resistance level it is then possible to isolate and measure typical physiological whole cell currents (>50 pA) that occur when the ion channels in the cell membrane are activated. The high electrical resistance seal also allows for the ability to control the voltage of the cell, a very useful feature in analyzing ion channel activity.

In order to achieve voltage clamp of the membrane, an electrode must be placed inside the cell. This requires that the part of the cell membrane 52 separating the two fluid chambers to be electrically permeabilized. This has been demonstrated in our device using voltage pulses ("zapping") utilizing the electrodes 34 and 40. It has also been demonstrated in our device by flowing proper concentrations of antibiotics (Nystatin or Amphotericin B) in the lower access chamber 38. There are also many other types of chemicals (e.g. gramicidin, ATP, valinomycin etc.) that could be used to provide electrical access to the cell interior. These would be apparent to one skilled in the art.

Preferred Hole Geometry

Typical mammalian cell lines of interest in ion channel expression systems are numerous but would include lines such as Chinese Hamster Ovary (CHO) or Human Embryo Kidney (HEK). These cells have mean diameters in the range of 10–20 μm. Optimum hole size in the substrate is governed by several considerations. Too large a hole can allow the cell to pass through the membrane hole (as opposed to sealing) when differential pressure is applied. In addition, it is observed that a larger hole diameter impedes higher seal resistances. On the other hand, a very small hole produces a higher electrical access resistance to the interior of the cell once an electrical seal is formed. This higher access resistance degrades the time resolution and voltage control performance of the system. Given these trade-offs, our preferred implementations feature hole diameters in the range of 2–4 μm, although a wider range of hole diameters (e.g. 1–10 μm) is feasible depending on cell type.

Given that the preferred hole diameter is on the order of a few micrometers, it is preferable that the unperforated substrate be thin (e.g. <25 μm), at least near the hole periphery. The reasons for this are several. Thick substrates introduce the problem of a very narrow pore relative to the substrate thickness which in turn makes it more difficult in achieving fluid access to the membrane. Fluid contact is necessary so as to provide an electrical pathway to measure the ion channel current, as well as to provide the cell with a normal physiological environment. Also, when attempting to gain electrical access to the interior of the cell, a long narrow channel derived from using a thick substrate will produce a higher electrical access resistance than that provided by a thinner film. As mentioned previously, a higher access resistance degrades system time resolution and the ability to voltage clamp the cell. In addition, any technique to machine the hole in the substrate is more difficult, time consuming and costly when starting with a thicker substrate. As such, substrate materials utilized in these embodiments had a thickness of less than 25 μm in their entirety or at least near the periphery of the hole.

Accordingly, a critical consideration of this invention is in the choice of the substrate used, the manner in which the substrate is processed to form the hole and the specific geometry utilized to make the concept workable in a high throughput instrument. With regards to the choice and manufacture of the substrate, two specific embodiments of the device have been demonstrated in our laboratory.

Substrate Embodiment 1—Thin Plastic Films

In one embodiment, thin plastic films were used as a substrate. Two types of thin films were tested, PET (Dupont Mylar) and polyimide (Dupont Kapton), although in principle one could utilize any thin plastic film (e.g. polycarbonate, polypropylene, polyethylene). The small diameter 2–4 μm holes were then photomachined into the plastic film using two processes.

Holes were first photo-machined using a pulsed YAG laser operating at 355 nm. In this arrangement, a single laser beam drills an isolated hole, one at a time. This beam is then scanned, typically using a galvanometric mirror scanning system to raster scan the incident beam over the substrate creating an array of photo-machined holes. Such systems often employ the use of an F-Theta lens system, which focuses as well as redirects the scanned laser beam so as to remain perpendicular to the target. The throughput of the scanning arrangement is thus governed by the time to drill one hole and the speed of the optical scanner.

Another photomachining process implemented involved using an excimer laser operating at 248 nm. These systems work by imaging a photo-mask onto the substrate and ablating the surface where the unmasked optical energy is allowed to pass through to the substrate. Using a proper mask design, the excimer imaging process can machine multiple holes in the substrate simultaneously. It is believed that this parallel machining process may provide a cost advantage in the large-scale production of such films. Data presented in this disclosure were gathered on substrates processed using the excimer laser system.

After the photo-machining process, the substrates were cleaned and subjected to a physical vapor deposition (PVD) of a silicon oxide SiO2 coating using an RF sputtering process. The process involved pumping the system down to ~4×10−6 torr using a cryo-pump, and subsequently back-filling the chamber with 7 mtorr of Argon. The high RF field generated between two electrode plates then interacts with the Argon to produce an ion bombardment of a SiO2 target. The dislodged SiO2 is then deposited onto the thin plastic film that is placed on a rotating platter running at 20 rpm. All operations are run at room temperature. Coating thicknesses implemented were in the range of 500 to 1000 angstroms.

It was experimentally determined that the SiO2 coating of the plastic film significantly enhanced the electrical sealing properties between the substrate and the cell membrane, increasing the seal resistance from tens of MΩ for the bare plastic film to resistances on the order of 1 GΩ with the deposited glass coating. It will be appreciated that other implementations of the coating process may be possible, such as using different thicknesses, different constituents (e.g. boron doped) as well as utilizing other potential deposition techniques including chemical vapor deposition. The specific implementation described here should not limit the scope of the invention.

Figure 3:
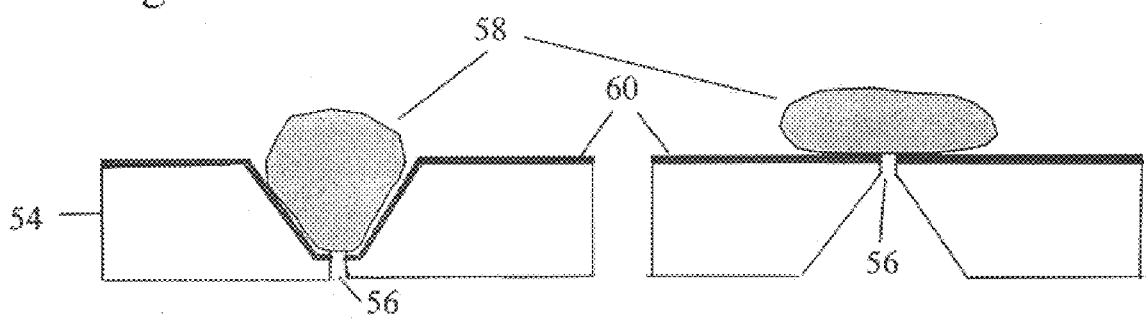
FIG. 3 shows a substrate hole geometry utilizing a thin plastic film.

FIG. 3 depicts two separate examples of a cell 58 positioned over a hole 56 in a thin layer substrate 54. As shown, due to the nature of the photomachining process, the holes are larger on one side than the other; the diameter on the smaller side of the pore is in the range of 2–4 μm. In each case a SiO2 coating 60 is applied to the cell-side surface to improve seal formation. Both geometries have proven to be viable in achieving good electrical resistance between the cell membrane and the substrate.

FIGS. 4 and 5 demonstrate typical whole-cell electrophysiological data acquired on CHO cells transfected with the voltage gated potassium channels Kv3.2. In this case the substrate material was Kapton, the hole was photomachined with an excimer laser (~3 μm diameter), and the resultant substrate was coated with a 500 angstrom SiO2 coating. The cell was positioned onto the hole in the substrate using differential pressure of approximately 5 inches of H20. After contacting the membrane, a seal resistance of approximately 1.3 GΩ was measured.

Figure 4A:
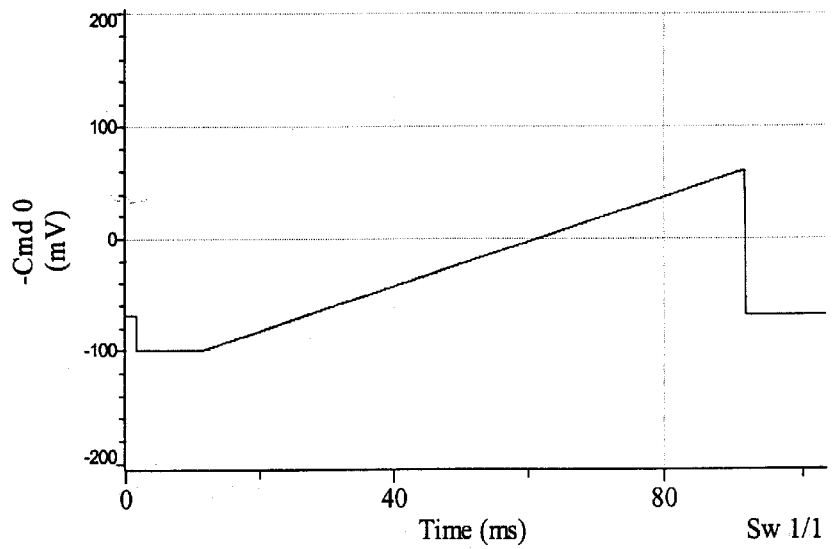
FIGS. 4a and 4b illustrates command voltage protocol and measured electrical leak resistance between a transfected CHO cell and a SiO2 coated kapton membrane pore.
Figure 4B:
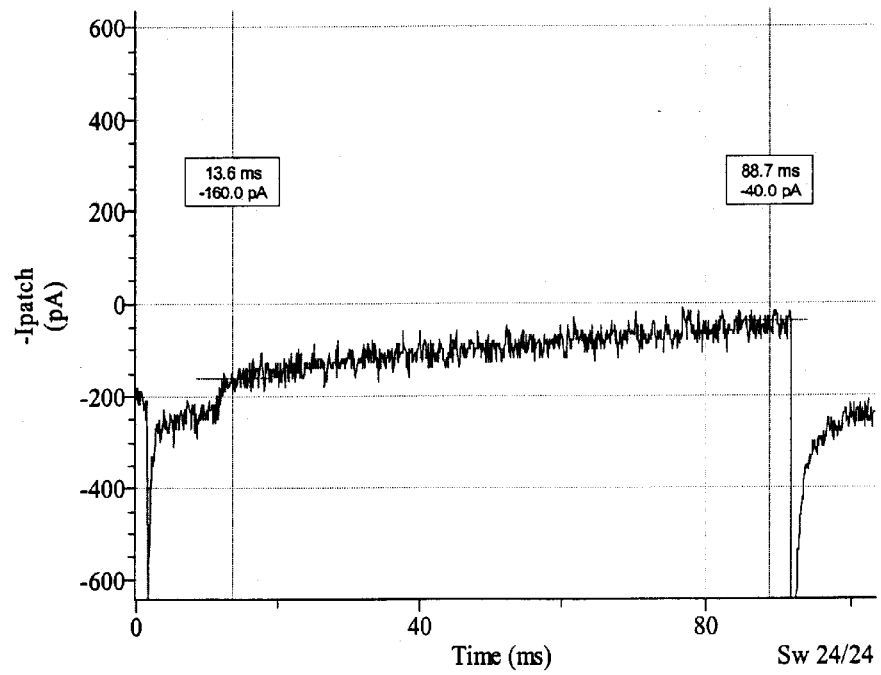

FIG. 4a and 4b contains two data graphs. FIG. 4a represents the applied command voltage placed on the measurement electrode. As shown, the voltage sweeps from −100 mV to +60 mV (range of 160 mV) over approximately a 90 msec time course. The measured current after the electrical seal was formed is shown on FIG. 4b. As shown the current over the same time course increased approximately 120 pA. Since the resistance of the cell membrane itself without ion channel activation is on the order of 10 GΩ, the measured current in this example is primarily due to leak resistance. The leak resistance, the measure of the electrical seal between cell membrane and the substrate, is computed from the figure as (160 mV/120 pA)=1.3 GΩ.

In order to demonstrate voltage control of the cell and physiological currents, the whole-cell configuration was implemented using the antibiotic amphotericin B to chemically permeabilize the part of the membrane covering the hole. This was accomplished by flowing amphotericin B at a concentration of 200 μg/ml to the underneath side of the hole. The mode of action of this compound is then to partition into cell membranes where it interacts with cholesterol to form tiny channels permeable to monovalent ions. This provides a low-resistance electrical access to the interior of the cell and in turn allows for control of the transmembrane voltage over the remaining unpermeabilized cell membrane.

Figure 5A:
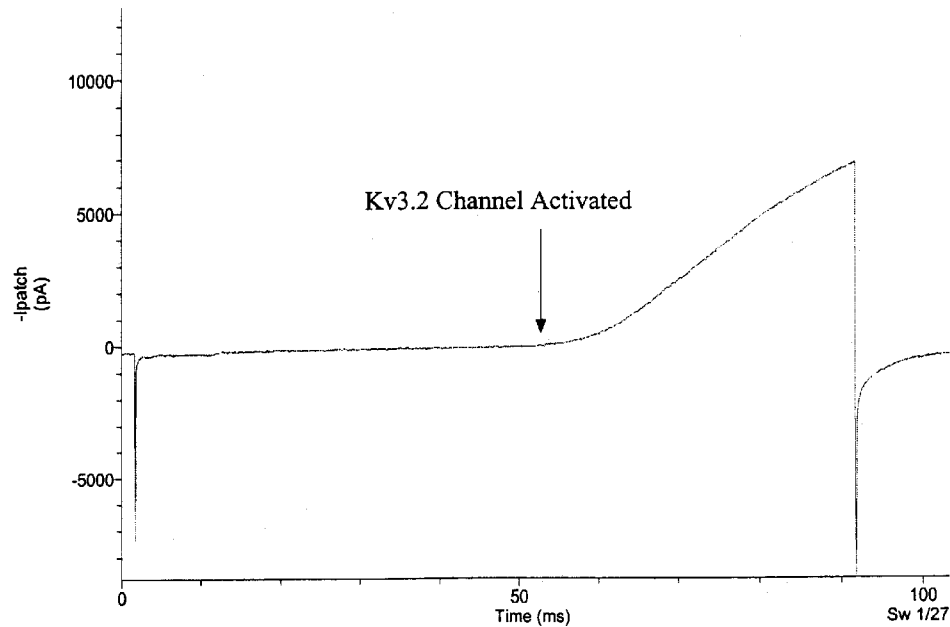
FIGS. 5a and 5b shows whole cell physiological currents measured on CHO cells transfected with the voltage-gated potassium channel Kv3.2: results of a voltage sweep from −100 mV to +60 mV, as well as a voltage step protocol from −70 mV to various step voltages.
Figure 5B:
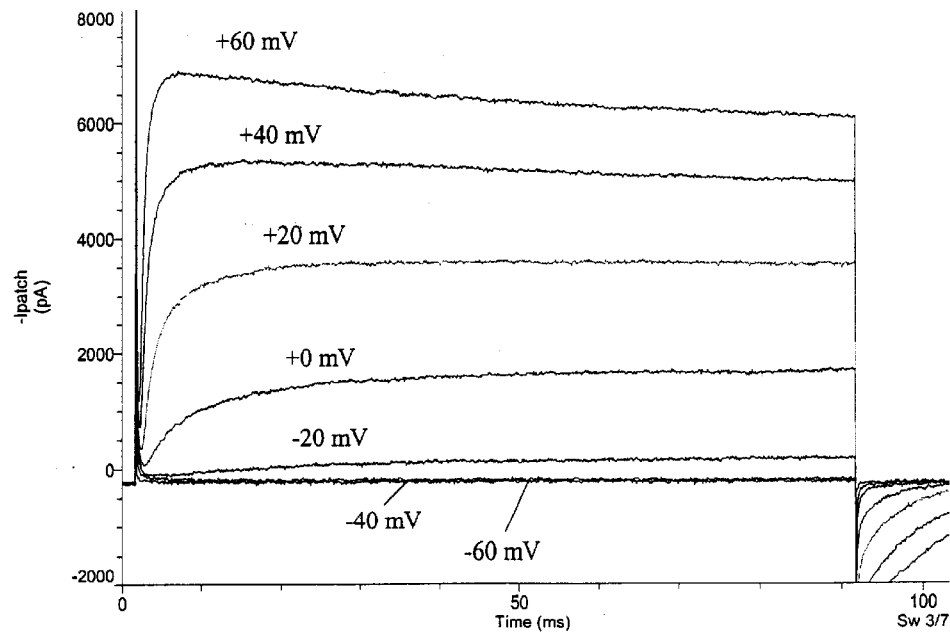

FIG. 5 demonstrates physiological measurement of the Kv3.2 channel activity after the application of amphotericin B and under "whole cell" conditions. In FIG. 5a an applied voltage sweep ranging from −100 V to +60 mV (same sweep as that of FIG. 4a) provides a measure of the voltage activity of the channel. As shown, there is practically no current present until approximately 50 msec into the sweep (transmembrane voltage of −10 mV), at which point the potassium channels open and a positive current (out of the cell) is recorded. The bottom half FIG. 5b is another representation of the channel activity where the voltage clamp was stepped sequentially for 90 msec intervals from a resting potential of −70 mV to the different respective voltages labeled on the graph. As shown, for this particular channel, current is slightly activated at a membrane potential of −20 mV, and is greatly activated at more positive potentials.

Although the data represented in FIG. 4 and 5 was gathered from a single cell on a single hole, the substrate, processing and experimental method utilized is entirely amenable to one where multiple cells could be measured in a parallel architecture.

Substrate Embodiment 2—Silicon

Another specific embodiment of the invention utilized standard solid-state process techniques to produce a perforate membrane. The processing started with <100> p-type silicon wafers that had been polished on both sides. After cleaning, a 4000 Å layer of silicone oxide (SiO2) was thermally grown on both sides of the wafer. This layer was then followed by a 2000 A layer of silicon nitride (Si3O4) and a second layer of 4000 Å SiO2, each of which were deposited using LPCVD on both sides. The front side of the wafer was then patterned with photoresist to allow for the removal of a 1 mm square section of all three oxide layers through Reactive Ion Etching (RIE). The back side of the wafer was then patterned to allow for the removal of a coincident 4 μm diameter section of the oxides, again through a reactive ion etch.

After stripping and cleaning, an anisotropic wet etch was performed in EDP to produce a pyramidal shaped hole from the front side of the wafer (1 mm square) to the oxide layers on the back side of the wafer. This resulted in a 1 μm thick, 300 μm square membrane of oxides with a 4 μm diameter hole in the center. This process may be extended to produce wafer substrates exhibiting 1 or 2-dimensional patterns of hundreds to thousands of holes. Individual cells were then positioned onto the individual etched holes using differential pressure as described previously.

System Architecture

A further important aspect of the invention is a system architecture enabling electrophysiological measurements to be conducted on a plurality of cells simultaneously. This involves the development of several subsystems that in concert provide the requisite functionality.

Figure 6:
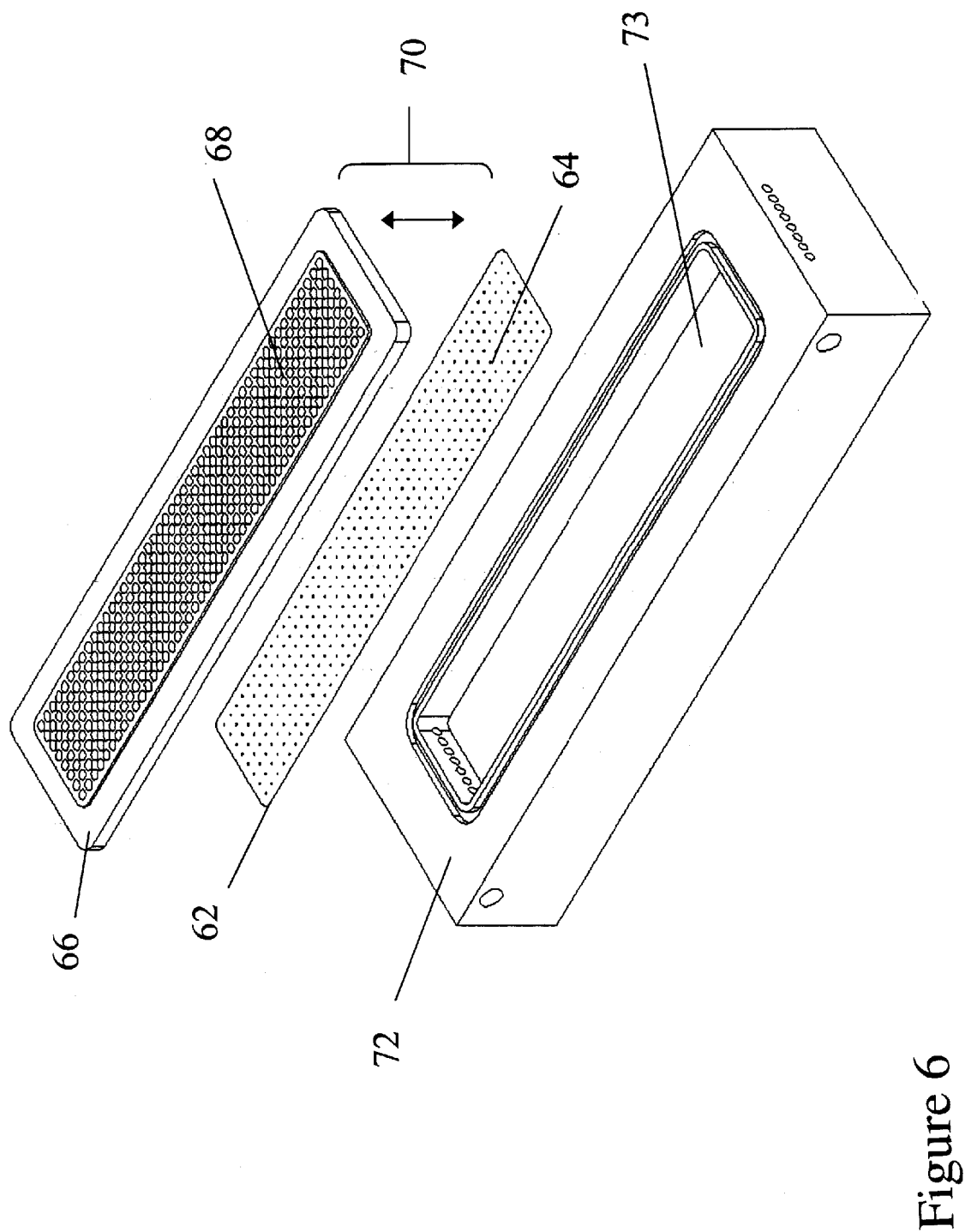
FIG. 6 shows a measurement substrate comprised of a polystyrene multi-well compartment adhered to a thin photo-machined plastic film. Also shown is the measurement platform (plenum) which accepts the measurement substrate during recording.

To perform a plurality of simultaneous cell measurements, it is advantageous to replicate hole fabrication onto one substrate, preferably using the above-described technologies. There are many possible implementations of such a replication, in one or two dimensions. A specific architecture is depicted in FIG. 6. In this implementation, each thin substrate 62 (e.g. Kapton film or silicon) is comprised of a rectangular array (48×8 shown) of individual photo machined holes 64 spaced a few millimeters apart. This substrate is then joined to a multi-well fixture 66 (e.g. injection molded polystyrene), which is comprised of an identical rectangular format (48×8) of individual wells 68. The purpose of the multi-well fixture is to provide isolated fluidics chambers for each individual hole. The thin substrate is joined to the multi-well fixture (e.g. by a non-toxic adhesive or ultrasonic bond) forming an electrically isolated fluid chamber on top of each isolated hole in the substrate. The entire fixture/substrate assembly will be referred to as the measurement substrate 70.

To use the measurement substrate in an instrument designed for parallel simultaneous measurements, it is necessary to be able to add suspended cells, cell membranes or microsphere beads with adherent cells into each respective well of the measurement substrate. The goal is to position one isolated cell or cell construct on top of each isolated hole in each individual well. Once added to each well, "cell positioning" is accomplished by applying differential pressure across the substrate to increase fluid flow through each hole. The cells or cell/bead constructs are then carried by the fluid flow to the single hole in each chamber, at which time an electrical seal can form.

A specific approach using differential pressure is depicted in FIG. 6, wherein the substrate 70 is locked into position onto a plenum 72. The purpose of the plenum is to provide an air-tight seal between the entire measurement substrate 70 and the plenum reservoir 73 as well as to provide fluid access to the bottom side of each hole in the membrane 62. The plenum is designed as a common fluidics reservoir tied to a pump system, whereas the reservoir fluid can be cycled enabling fluid constituents in the reservoir to be altered, e.g. the aforementioned addition of a chemical for electrical permeabilization of the membrane.

Because of the air tight seal, the fluid in the plenum reservoir may be maintained at slightly less than atmospheric pressure thereby introducing a differential pressure across the membrane and in turn forcing fluid flow from the top chamber through each individual hole and into the common lower reservoir. This flow causes individual suspended cells (or cell membranes) in the multi-well compartments 68 to be pulled down onto the individual membrane holes 64 in parallel and without direct human intervention. In addition, once the cells contact the membrane surface, the continued use of differential pressure has been found to enhance the formation of high-resistance electrical seals between the substrate material and the cell membrane.

While introducing physiological buffer solution to the underneath side of the membrane is accomplished by the plenum system, a separate fluidic system is required for the top. Fluid access to the top of the measurement substrate is convenient for the following functions:

The introduction of physiological saline buffer to each of the multi-well chambers 68;

The introduction of suspended cells, cell membranes, or cells adhered to beads into the multi-well chambers; and The introduction of experimental chemical entities to the multi-well chambers 68 for the purpose of analyzing their effect on the electrophysiology of the biological membrane.

Figure 7:
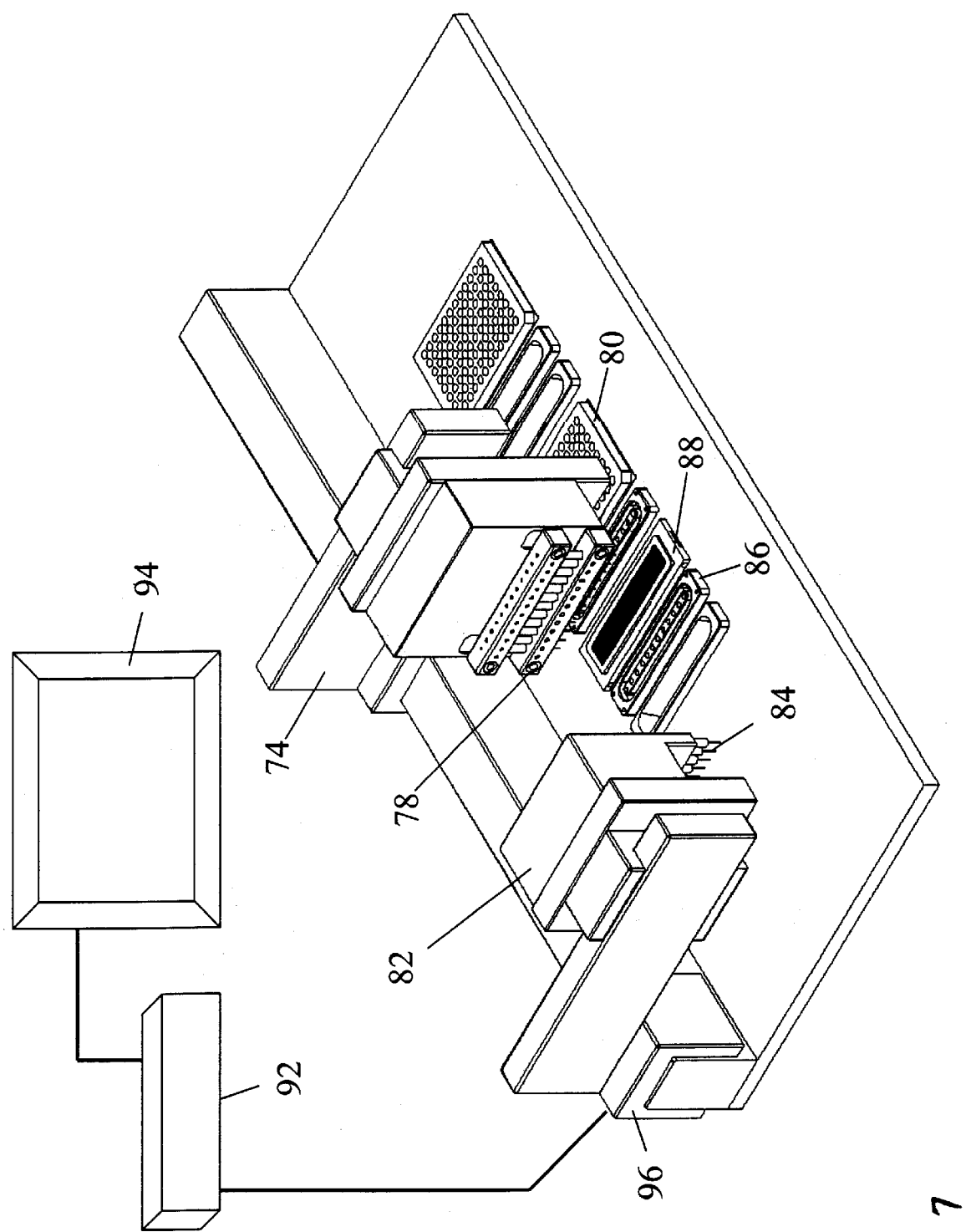
FIG. 7 shows a high throughput screening system depicting a complete functional measurement platform including an integrated electronics head for parallel electrical measurements, an integrated fluidics head for parallel fluid additions, as well computer display and control.

All of the functions above lend themselves to a fluidics system that aspirates fluid from a source reservoir or multiwell plate and then dispenses the same fluid in a destination reservoir. In its simplest configuration, the fluidic system may be implemented using a single pipette channel, whereby fluid is transferred from a source reservoir to one destination well at a time. FIG. 7 depicts a system architecture for the instrument, wherein the integrated fluidics head is comprised of a mechanical position element 74 and a twelve-channel pipette head 78. The mechanical positioning element produces the 2 or 3 dimensional positioning of either fluidics head over the various fluid reservoirs of the system as needed.

As an example, potential drug candidates are often stored in solution in multi-well plates 80. At the appropriate time in the experimental cycle, these chemical entities must be transferred into the measurement substrate. In the depiction given in FIG. 7, this is accomplished for 12 wells simultaneously by aspirating fluid from the drug plate and in turn dispensing the drugs into the appropriate measurement substrate wells 88. Obviously there are many potential variations of the fluidics architecture chosen, e.g. using a two dimensional (nxm) multi-channel pipette as opposed to the one dimensional 12 position head shown.

Consistent with the aforementioned description, in order to make the electrophysiogical measurements on the cells, an electrical circuit must be implemented across each individual substrate hole. This requires a sense electrode on one side of the membrane and a ground electrode on the other. A specific implementation of such an architecture is again depicted in FIG. 7, whereby an electronics head element 82 consisting of 12 individual measurement probes 84 each capable of functioning as the sensing electrode for 12 individual wells of the measurement substrate simultaneously.

The head is capable of two- or three-dimensional motion enabling it to move between the various wells of the measurement substrate as well as to a wash station 86 where the individual sensing electrodes can be washed between experimental runs. Each sensing electrode is tied to its own high impedance amplifier arrangement consistent with that necessary for such measurements and is located in the electronics head housing. The analog output signals for each of the respective output amplifiers is then digitized by appropriate analog to digital (A/D) converters and transferred to computer for further processing. As with the fluidics system, there are many potential variations of the electronics architecture, e.g. using an implementation involving a larger number or array (nxm) of sensing electrodes.

Each individual circuit is completed by the addition of saline solution in each individual well of the measurement substrate above the membrane as well as by the introduction of saline solution below the membrane via the plenum 88. A common ground electrode is located in the plenum fluid reservoir thereby completing the measurement circuit.

The entire system is controlled via an external microcomputer 92, CRT display 94 and software user interface. A useful implementation incorporates an imbedded microcontroller 96 interfaced to the external PC, which would control all the real-time functional aspects of the instrument including the motion control, fluidics control, as well as the electrical data recording.

REFERENCES

[1] Denyer, J., Worley J., Cox B., Allenby G., and Banks M., HTS Approaches to Voltage-gated Ion Channel Drug Discovery, *Drug Discovery Today*, Vol. 3., No. 7, July 1998, pp. 323–332.

[2] Ausubel, F. M., Brent, R., Kingston, R. E., Moore, D. D., Seidman, J. G., Smith, J. A., and Struhl, K. (eds.), 1987, *Current Protocols in Molecular Biology*, John Wiley & Sons, New York.

[3] Berger, S. L., and Kimmel, A. R. (eds.), 1987, *Guide to Molecular Cloning Techniques*, Academic Press, San Diego.

[4] Kelly M. L., Woodbury D. J., Ion channels from synaptic vesicle membrane fragments reconstituted into lipid bilayers, Biophysical Journal, Vol. 70, pp2593–2599.

[5] Neher E., Sakmann B., Single channel currents recorded from membrane of denervated frog muscle fibers. 1976 *Nature* 260: 799–802.

[6] Neher E., Sakmann B., Steinbach J. H., (1978) The Extracellular Patch Clamp: A method for resolving currents through individual open channels in biological membranes. *Pflugers Arch* 375: 219–228.

[7] Hammill O. P., Marty A., Neher E., Sakmann B., and Sigworth F. J., (1981) Improved Patch-Clamp Techniques for High-Resolution Current Recording from Cells and Cell-Free Membrane Patches, *Pflugers Arch* 391:85–100.

[8] Sherman-Gold, Rivka (ed.) 1993, The Axon Guide for Electrophsiology & Biophysics.

[9] Rae, J., Cooper K., Gates P., Watsky, M., Low access resistance perforated patch recordings using amphotericin B, *Journal of Neuroscience Methods*, 37 (1991) pp. 15–26.

[10] Sakmann B., Neher E. (eds.) 1995, Single-Channel Recording, $2^{nd}$ Edition, Plenum Press, NY.

We claim:

1. Electrophysiological measurement apparatus, comprising:
   a first fluid chamber containing a cell or membrane to be measured;
   a second fluid chamber;
   a thin plastic substrate separating the two chambers, the substrate having an aperture formed therethrough which is smaller in diameter than the cell or membrane, thereby enabling a high-resistance seal to be formed between the cell or membrane and the substrate;
   the substrate further including a glass coating at least in the region where the high-resistance seal is formed between the cell or membrane and the substrate;
   an electrode disposed in each of the fluid chambers; and
   electrophysiological measurement circuitry in electrical communication with the electrodes.

2. The electrophysiological measurement apparatus of claim 1, including a single aperture formed in the substrate separating the first and second chambers.

3. The electrophysiological measurement apparatus of claim 1, wherein the substrate is PET (mylar) or polyimide.

4. The electrophysiological measurement apparatus of claim 1, wherein the aperture is in the range of 1 to 10 micrometers.

5. The electrophysiological measurement apparatus of claim 1, wherein the aperture is tapered.

6. The electrophysiological measurement apparatus of claim 1, wherein a differential pressure is applied between the first and second chambers causing the cell or membrane to migrate to the aperture.

7. As The electrophysiological measurement apparatus of claim 1, wherein a differential pressure is maintained between the first and second chambers until the high-resistance is formed between the cell or membrane and the substrate.

8. The electrophysiological measurement apparatus of claim 1, wherein the second fluid chamber includes a chemical reagent which electrically permeabilizes the biological membrane in the vicinity of the aperture.

9. The electrophysiological measurement apparatus of claim 1, wherein a high voltage is temporarily applied across the electrodes to permeabilize the biological membrane in the vicinity of the aperture.

10. The electrophysiological measurement apparatus of claim 1, further including:
    a plurality of first chambers forming a multi-well plate;
    a substrate having a plurality of apertures; and
    wherein the substrate is bonded to the multi-well plate such that the apertures are in alignment with the chambers thereof.

11. The electrophysiological measurement apparatus of claim 10, further including:
    a mechanism for moving the electrode into the chambers of the multi-well plate so as to automate the measurement of the cells or membranes contained therein.

12. The electrophysiological measurement apparatus of claim 10, further including:
    a plurality of electrodes in alignment with a plurality of the chambers of the multi-well plate; and
    a mechanism for moving the electrodes into the chambers of the multi-well plate to perform simultaneous measurements on the cells or membranes contained therein.

13. Electrophysiological measurement apparatus, comprising:
    a multi-well plate having a plurality of fluid chambers, each containing biological material to be measured;
    a thin substrate having an array of apertures in alignment with the chambers of the multi-well plate;
    the substrate being bonded to the multi-well plate such that the chambers are open at the top and sealed at the bottom except for the apertures;
    the apertures being smaller in diameter than the biological material, thereby enabling a high-resistance seal to be formed between the material in each chamber and a corresponding aperture;
    a fluid plenum to receive the multi-well plate such that one side of the substrate is immersed;
    a first electrode disposed in the fluid plenum;
    at least one second electrode moveable into the top openings of the fluid chambers of the multi-well plate; and
    electrophysiological measurement circuitry in electrical communication with the electrodes.

14. The electrophysiological measurement apparatus of claim 13, including a single aperture associated with each chamber of the multi-well plate.

15. The electrophysiological measurement apparatus of claim 13, wherein the substrate is a plastic substrate having a glass coating at least in the region where the high-resistance seal is formed between the material and the substrate.

16. The electrophysiological measurement apparatus of claim 13, wherein the substrate is poly(ethylene terephthalate) (PET) or polyimide.

17. The electrophysiological measurement apparatus of claim 13, wherein the diameter of the apertures is in the range of 1 to 10 micrometers.

18. The electrophysiological measurement apparatus of claim 13, wherein the apertures are tapered.

19. The electrophysiological measurement apparatus of claim 13, wherein the multi-well plate is sealed to the fluid plenum, enabling a differential pressure to be applied relative to the fluid in each chamber, thereby causing the material in each chamber to migrate to a respective aperture.

20. The electrophysiological measurement apparatus of claim 13, wherein the multi-well plate is sealed to the fluid plenum, enabling a differential pressure to be maintained relative to the fluid in each chamber until between the material in each chamber forms the high-resistance seal to the corresponding aperture.

21. The electrophysiological measurement apparatus of claim 13, wherein the fluid plenum includes a chemical reagent causing the material in each chamber to electrically permeabilize in the vicinity of the aperture.

22. The electrophysiological measurement apparatus of claim 13, wherein a high voltage is temporarily applied across the electrodes to permeabilize the material in each chamber, at least in the vicinity of the apertures.

23. The electrophysiological measurement apparatus of claim 13, further including:
    a mechanism for moving the electrode into the chambers of the multi-well plate so as to automate the measurement of the material contained therein.

24. The electrophysiological measurement apparatus of claim 13, further including:
    a plurality of electrodes in alignment with a plurality of the chambers of the multi-well plate; and a mechanism for moving the electrodes into the chambers of the multi-well plate to perform simultaneous measurements on the material contained therein.

25. The electrophysiological measurement apparatus of claim 13, further including:

a system for transferring fluids from one or more sources to the chambers of the multi-well plate.

26. Electrophysiological measurement apparatus, comprising:

a plurality of first fluid chambers forming a multi-well plate, each first fluid chamber containing a cell or membrane to be measured;

a second fluid chamber;

a thin substrate separating the two chambers, the substrate having a plurality of apertures formed therethrough and bonded to the multi-well plate such that each one of the apertures is in alignment with one of the first fluid chambers;

the apertures being smaller in diameter than the cells or membranes, thereby enabling a high-resistance seal to be formed between each cell or membrane and the substrate;

a moveable electrode; and electrophysiological measurement circuitry in electrical communication with the electrodes, including a mechanism for moving the electrode into the chambers of the multi-well plate so as to automate the measurement of the cells or membranes contained therein.

27. The electrophysiological measurement apparatus of claim 26, including a single aperture associated with each one of the first fluid chambers.

28. The electrophysiological measurement apparatus of claim 26, wherein the substrate is a plastic substrate having a glass coating at least in the region where the high-resistance seal is formed between the cell or membrane and the substrate.

29. The electrophysiological measurement apparatus of claim 28, wherein the substrate is poly(ethylene terephthalate) (PET) or polyimide.

30. The electrophysiological measurement apparatus of claim 26, wherein the diameter of each aperture is in the range of 1 to 10 micrometers.

31. The electrophysiological measurement apparatus of claim 26, wherein each aperture is tapered.

32. The electrophysiological measurement apparatus of claim 26, wherein a differential pressure is applied between the first and second chambers causing the cells or membranes to migrate to the apertures.

33. The electrophysiological measurement apparatus of claim 26, wherein a differential pressure is maintained between the first and second chambers until the high-resistance is formed between the cells or membranes and the substrate.

34. The electrophysiological measurement apparatus of claim 26, wherein the second fluid chamber includes a chemical reagent which electrically permeabilizes the biological membranes in the vicinity of the aperture.

35. The electrophysiological measurement apparatus of claim 26, wherein a high voltage is temporarily applied across the electrodes to permeabilize the biological membrane in the vicinity of the apertures.

36. Electrophysiological measurement apparatus, comprising:

a plurality of first fluid chambers forming a multi-well plate, each first fluid chamber containing a cell or membrane to be measured;

a second fluid chamber;

a thin substrate separate separating the two chambers, the substrate having a plurality of apertures formed therethrough and bonded to the multi-well plate such that each one of the apertures is in alignment with one of the first fluid chambers;

the apertures being smaller in diameter than the cells or membranes, thereby enabling a high-resistance seal to be formed between the cell or membrane and the substrate;

a plurality of electrodes in alignment with a plurality of the chambers of the multi-well plate; and a mechanism for moving the electrodes into the chambers of the multi-well plate to perform simultaneous measurements on the cells or membranes contained therein.

37. The electrophysiological measurement apparatus of claim 36, including a single aperture associated with each one of the first fluid chambers.

38. The electrophysiological measurement apparatus of claim 36, wherein the substrate is a plastic substrate having a glass coating at least in the region where the high-resistance seal is formed between the cell or membrane and the substrate.

39. The electrophysiological measurement apparatus of claim 38, wherein the substrate is poly(ethylene terephthalate) (PET) or polyimide.

40. The electrophysiological measurement apparatus of claim 36, wherein each aperture is in the range of 1 to 10 micrometers.

41. The electrophysiological measurement apparatus of claim 36, wherein each aperture is tapered.

42. The electrophysiological measurement apparatus of claim 36, wherein a differential pressure is applied between the first and second chambers causing the cells or membranes to migrate to the apertures.

43. The electrophysiological measurement apparatus of claim 36, wherein a differential pressure is maintained between the first and second chambers until the high-resistance is formed between the cells or membranes and the substrate.

44. The electrophysiological measurement apparatus of claim 36, wherein the second fluid chamber includes a chemical reagent which electrically permeabilizes the biological membranes in the vicinity of the aperture.

45. The electrophysiological measurement apparatus of claim 36, wherein a high voltage is temporarily applied across the electrodes to permeabilize the biological membrane in the vicinity of the apertures.

* * * * *

UNITED STATES PATENT AND TRADEMARK OFFICE
CERTIFICATE OF CORRECTION

PATENT NO.    : 6,488,829 B1
DATED         : December 3, 2002
INVENTOR(S)   : Kirk S. Schroeder et al.

It is certified that error appears in the above-identified patent and that said Letters Patent is hereby corrected as shown below:

<u>Title page,</u>
Please insert item:
-- [73]   Assignee:   Essen Instruments, Inc., Ann Arbor, MI (US) --;

<u>Column 7,</u>
Line 58, delete "The bottom half".

Signed and Sealed this

Tenth Day of February, 2004

JON W. DUDAS
*Acting Director of the United States Patent and Trademark Office*